(12) United States Patent
Park

(10) Patent No.: US 11,147,769 B2
(45) Date of Patent: Oct. 19, 2021

(54) COMPOSITION FOR PREVENTING HAIR LOSS AND THICKENING HAIR AND PREPARATION METHOD THEREOF

(71) Applicants: DERMA CENTRIC INC., Seoul (KR); Jun Bum Park, Seoul (KR)

(72) Inventor: Jun Bum Park, Seoul (KR)

(73) Assignee: DERMA CENTRIC INC., Seoul (KR)

( * ) Notice: Subject to any disclaimer, the term of this patent is extended or adjusted under 35 U.S.C. 154(b) by 0 days.

(21) Appl. No.: 16/892,745

(22) Filed: Jun. 4, 2020

(65) Prior Publication Data
US 2020/0383921 A1 Dec. 10, 2020

(30) Foreign Application Priority Data
Jun. 7, 2019 (KR) .................. 10-2019-0067573

(51) Int. Cl.
| | |
|---|---|
| A61K 9/16 | (2006.01) |
| A61K 47/38 | (2006.01) |
| A61K 47/46 | (2006.01) |
| A61K 47/42 | (2017.01) |
| A61K 47/18 | (2017.01) |
| A61K 47/32 | (2006.01) |
| A61K 31/045 | (2006.01) |
| A61K 31/60 | (2006.01) |
| A61K 31/164 | (2006.01) |
| A61K 31/455 | (2006.01) |
| A61K 33/30 | (2006.01) |
| A61K 31/407 | (2006.01) |
| A61P 17/14 | (2006.01) |
| A61K 47/36 | (2006.01) |
| A61M 35/00 | (2006.01) |

(52) U.S. Cl.
CPC .......... *A61K 9/1652* (2013.01); *A61K 31/045* (2013.01); *A61K 31/164* (2013.01); *A61K 31/407* (2013.01); *A61K 31/455* (2013.01); *A61K 31/60* (2013.01); *A61K 33/30* (2013.01); *A61K 47/183* (2013.01); *A61K 47/32* (2013.01); *A61K 47/36* (2013.01); *A61K 47/38* (2013.01); *A61K 47/42* (2013.01); *A61K 47/46* (2013.01); *A61P 17/14* (2018.01); *A61M 35/003* (2013.01)

(58) Field of Classification Search
None
See application file for complete search history.

(56) References Cited

FOREIGN PATENT DOCUMENTS

| KR | 20150061234 | 6/2015 |
|---|---|---|
| KR | 20160149356 | 12/2016 |
| KR | 20160149356 A | * 12/2016 |

* cited by examiner

*Primary Examiner* — Jessica Worsham
(74) *Attorney, Agent, or Firm* — Cantor Colburn LLP

(57) ABSTRACT

Provided is a composition for reducing hair loss and thickening hair and a preparation method thereof, and more particularly to a composition for preventing hair loss and thickening hair that includes beads composed of carrageenan, cellulose, agar, charcoal powder, acrylate copolymer, caffeine, amino acid, keratin, gellan gum, *Ulva lactuca* powder, menthol, salicylic acid, dexpanthenol, niacinamide, zinc pyrithione, biotin, etc.

9 Claims, 1 Drawing Sheet

COMPOSITION FOR PREVENTING HAIR LOSS AND THICKENING HAIR AND PREPARATION METHOD THEREOF

BACKGROUND OF THE INVENTION

(A) Field of the Invention

The present invention relates to a composition for reducing hair loss and thickening hair and a preparation method thereof, and more particularly to a composition for preventing hair loss and thickening hair that includes beads composed of carrageenan, cellulose, agar, charcoal powder, acrylate copolymer, caffeine, amino acid, keratin, gellan gum, *Ulva lactuca* powder, menthol, salicylic acid, dexpanthenol, niacinamide, zinc pyrithione, biotin, etc.

(B) Description of the Related Art

All around the world, various research studies are underway to explore the way to promote hair growth and treat hair loss related to the genetic or environmental factors and incurring psychological distress in today's society that attaches importance to beauty.

The number of hairs on the human head is roughly estimated at 100,000 to 150,000. Each strand of hair follows a specific growth cycle that repeats three stages: anagen phase, the hair growth phase where the hair grows; catagen phase where the hair maintains its shape, yet with a reduced rate of metabolism, at the end of the anagen phase; and finally telogen phase where derma papilla and follicles shrink gradually to push out the hair bulb. The growth cycle and lifespan of the hair may vary depending on a variety of factors, including nutritional status, health history, heredity, hormone change, aging, and so forth. The patients with a hair loss issue experience rapid shifts from the anagen phase to the catagen and telogen phases to shorten the anagen phase relatively, which causes more hair to shed in an abnormal fashion and hair follicles to miniaturize and fall out.

The biggest culprit of hair loss is a combination of genetics and male sex hormone (androgen). First of all, the hair loss is due to a genetic predisposition, and whether it is incurred or not depends on the male sex hormone. The major male sex hormone most critical to hair loss is dihydrotestosterone (DHT), an active androgen activated by the enzyme 5-alpha-reductase. There are also other factors believed to be involved in hair loss: stress, disease, childbirth, dietary changes, irregular routine of life, bad blood circulation, infectious inflammation, peroxides, etc. The cause of hair loss is still unclear from a medical perspective. Without a clear cause, it may be actually difficult to accommodate people's needs for the immediate effect to reduce hair loss and thicken the hair.

BRIEF SUMMARY OF THE INVENTION

Technical Problem

For solving the problems with the prior art, it is an object of the present invention to provide a composition containing beads as an active ingredient for reducing hair loss and thickening hair and a preparation method thereof.

Technical Solution

To achieve the object of the present invention, there is provided a composition for preventing hair loss and thickening hair that includes a bead as an active ingredient, where the bead includes 1.0 to 2.0 wt. % of carrageenan, 0.1 to 1.0 wt. % of cellulose, 0.1 to 2.0 wt. % of agar, 0.01 to 0.5 wt. % of charcoal powder, 0.1 to 1.0 wt. % of acrylate copolymer, 0.01 to 1.0 wt. % of caffeine, 0.01 to 0.5 wt. % of amino acid, 0.01 to 1.0 wt. % of keratin, purified water, and a thickening agent.

In the present invention, the bead may further include at least one active ingredient selected from the group consisting of *Ulva lactuca* extract powder, L-menthol, salicylic acid, dexpanthenol, niacinamide, zinc pyrithione, and biotin.

In the present invention, the composition may include a bead and a gel, where the bead is contained in an amount of 3 to 10 wt. % with respect to 100 wt. % of the composition.

In the present invention, the gel may include 1.5 wt. % of glyceryl glucoside, 0.2 wt. % of panthenol, 0.1 wt. % of disodium Edta, 3.0 wt. % of butylene glycol, 0.45 wt. % of aminomethylpropanol, 0.5 wt. % of acrylate, 0.5 wt. % of a preservative, 0.3 wt. % of menthol, 0.25 wt. % of salicylic acid, 10.0 wt. % of ethanol, 1.5 wt. % of PEG-60 hydrogenated castor oil, 1.5 wt. % of polysorbate 80, and purified water.

In the present invention, the bead may have an average diameter of 4 to 10 mm and an average hardness of 400 to 700 g, where the bead is forced to pass through a mesh with a mesh area of 0.25 to 1 $mm^2$ and lose its own shape and thus mixed with the gel.

In the present invention, the composition may be provided as a formulation type selected from the group consisting of, if not limited to, hair toner, hair lotion, hair cream, hair spray, hair mousse, hair gel, hair soap, hair shampoo, hair conditioner, hair massage pack, and hair treatment.

To achieve the objects of the present invention, there is also provided a method for preparing a composition for preventing hair loss and thickening hair that includes a bead as an active ingredient, where the bead is prepared in the steps of: (a1) mixing, with respect to 100 wt. % of the bead, 1.0 to 2.0 wt. % of carrageenan, 0.1 to 1.0 wt. % of cellulose, 0.1 to 2.0 wt. % of agar, 0.01 to 0.5 wt. % of charcoal powder, 0.1 to 1.0 wt. % of acrylate copolymer, 0.01 to 1.0 wt. % of caffeine, 0.01 to 0.5 wt. % of amino acid, and 0.01 to 1.0 wt. % of keratin, with purified water to obtain a mixture and homogenizing the mixture under agitation at 70° C.; (a2) dropping the homogenized mixture on cold oil through a fog nozzle to form a bead; and (a3) washing the bead with purified water.

The present invention also provides a method for preparing a composition for preventing hair loss and thickening hair that includes: (b1) mixing, with respect to 100 wt. % of gel, 1.5 wt. % of glyceryl glucoside, 0.2 wt. % of panthenol, 0.1 wt. % of disodium Edta, 3.0 wt. % of butylene glycol, and 0.45 wt. % of aminomethylpropanol with purified water to obtain a mixture and homogenizing the mixture under agitation at 70° C. to prepare a homogenized mixture 1; (b2) adding 0.5 wt. % of acrylate with respect to 100 wt. % of the gel to the homogenized mixture 1 under sustained agitation at 70° C. to prepare a homogenized mixture 2; (b3) adding, with respect to 100 wt. % of the gel, 0.5 wt. % of a preservative, 0.3 wt. % of menthol, 0.25 wt. % of salicylic acid, 10.0 wt. % of ethanol, 1.5 wt. % of PEG-60 hydrogenated castor oil, 1.5 wt. % of polysorbate 80, and purified water and mixing under sustained agitation to form a gel; and (b4) adding beads to the gel and uniformly mixing the beads and the gel together.

In the method for preparing a composition for preventing hair loss and thickening hair according to the present invention, the bead may have an average diameter of 6 to 10 mm and an average hardness of 400 to 700 g, which bead is forced to pass through a mesh with a mesh area of 0.25 to 1 mm² and lose its shape and thus mixed with the gel.

The present invention also provides a container for holding a composition for preventing hair loss and thickening hair, where the container includes a composition holding portion 10, a composition mixing portion 20, and a composition discharging portion 30. The composition holding portion 10 includes a bead 11 and a gel 12 with a specific gravity difference of 0 or 0.1 or less. The composition mixing portion 20 includes a fixed mesh positioned perpendicular to a discharging direction. The composition discharging portion 30 includes an airless pumping portion.

In the container of the present invention, the bead may have an average diameter of 6 to 10 mm and an average hardness of 400 to 700 g, which bead is forced to pass through a mesh with a mesh area of 0.25 to 1 mm² and lose its shape and thus mixed with the gel.

Effects of Invention

In the composition of the present invention, carrageenan, cellulose, agar, charcoal powder, acrylate copolymer, caffeine, amino acid, keratin, and gellan gum are used to form a physical coating on the hair and increase the thickness of the hair, and menthol, salicylic acid, dexpanthenol, niacinamide, zinc pyrithione, and biotin help protect the scalp to reduce hair loss.

DETAILED DESCRIPTION OF THE INVENTION

Figure 1:
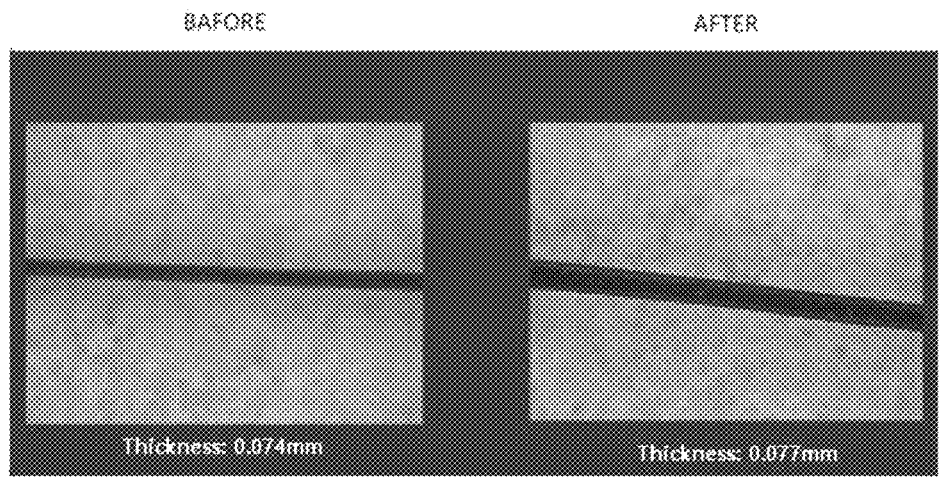
FIG. 1 shows a comparison of the thickness of hair before and 2 weeks after the application of a hair essence containing the composition of the present invention.

The present invention is to provide a composition for preventing hair loss and thickening hair that includes a bead as an active ingredient, where the bead includes 1.0 to 2.0 wt. % of carrageenan, 0.1 to 1.0 wt. % of cellulose, 0.1 to 2.0 wt. % of agar, 0.01 to 0.5 wt. % of charcoal powder, 0.1 to 1.0 wt. % of acrylate copolymer, 0.01 to 1.0 wt. % of caffeine, 0.01 to 0.5 wt. % of amino acid, 0.01 to 1.0 wt. % of keratin, purified water, and a thickening agent.

Carrageenan, a complex polysaccharide extracted from red edible seaweeds living in uncontaminated areas of the sea, is used in the food applications as a dispersing agent, an emulsion stabilizer, a swelling agent, a thickening agent, a binding agent, dietary fiber, an anti-crystallizing agent, a gelling agent, or the like. It is generally an anionic polymer containing highly hydrophilic sulfate groups. Five classes of carrageenan are available depending on the content and position of the sulfate groups, termed kappa-, lambda-, iota-, mu-, and furcellaran-carrageenan, which carrageenans are commercially available alone or in combination. In the present invention, carrageenan is used as a stabilizer and a dispersing agent and contained in an amount of 1.0 to 2.0 wt. % with respect to the total weight of the polymer bead. The content of carrageenan less than 1.0 wt. % renders the bead so hard as to lose the bead shape while passing through a mesh, thus the bead cannot be well mixed with the gel component. The content of carrageenan greater than 2.0 wt. % reduces the hardness of the bead extremely that the bead cannot maintain its shape during the filling process.

Cellulose, also called cellulose fiber, is a natural polymer with D-glucose units (six-membered rings) connected by β-1,4 glycosidic bonds. Depending on its source, cellulose can be classified into plant cellulose and microbial/animal cellulose. The plant cellulose is derived from plant sources, such as wood timber, bamboo, hemp, jute, kenaf, cotton, crops, vegetable foods, etc. The microbial/animal cellulose is produced by microorganisms including bacteria or animals, such as *cladophora*, glaucocystis, *valonia*, tunicate, etc. Celluloses are used in large quantities for paper or textile fibers, and cellulose derivatives are available in a variety of applications, including plastics, adhesives, films, foaming agents, etc. In the present invention, cellulose is used as a thickening agent in an amount of 0.1 to 1.0 wt. %, preferably 0.4 to 0.6 wt. %, with respect to the total weight of the polymer bead. The content of cellulose less than 0.1 wt. % is not enough for the cellulose to serve as a thickening agent and causes a reduction in the hair thickening effect due to a reduced amount of the bead adsorbed to the hair. The content of cellulose greater than 1.0 wt % results in the difficulty of forming beads.

Agar is vegetable gelatin derived from edible seaweed, *gelidium amansii*, also known as umutgasari, and dried by freeze dehydration or press dehydration. It consists of 15% water, 2% protein, 3.5% ash, 0.5% fat, and mostly two polysaccharides: 70% agarose (neutral polysaccharide) and 30% agaropectin (acidic polysaccharide). The main usage of agar is a gelling agent for foods. In the present invention, agar is used in an amount of 0.1 to 2.0 wt. %, preferably 0.5 to 0.8 wt. % with respect to the total weight of the polymer bead. The content of agar less than 0.1 wt. % leads to a reduction in the hair thickening effect due to a reduced amount of the bead adsorbed to the hair. The content of agar greater than 2.0 wt. % renders the bead extremely hard to apply to the hair.

Charcoal powder is made from normal wood, preferably pinewood, bamboo or oak wood, particularly bamboo plants by means of a known method, for example, burning with temperature of 500° C. or above, preferably 700 to 1,500° C. and grinding into fine powder. It is a porous, odorless, flavorless, innocuous powder with weak alkalinity used to provide elasticity, extendibility and adhesion ability for the polymer bead. In the present invention, the charcoal powder is used in an amount of 0.01 to 0.5 wt. %, preferably 0.09 to 0.12 wt. % with respect to the total weight of the polymer bead. The content of charcoal powder less than 0.01 wt. % causes deterioration in the adhesion ability to the hair and reduces the hair thickening effect. The content of charcoal powder greater than 0.5 wt. % results in the difficulty of forming beads.

Acrylate copolymer is a copolymer of monomers consisting of acrylate ($CH_2$=$CR^1$—$COOR^2$), acrylic acid ($CH_2$=$CR^3$—$COOH$), or one of their salts, where $R^1$ and $R^2$ are independently selected from H, $CH_3$, or $C_2H_5$; and $R^2$ is selected from $C_{1-10}$ alkyl groups. It is chiefly used as a hair setting agent. In the present invention, the acrylate copolymer is contained in an amount of 0.1 to 1.0 wt. %, preferably 0.2 to 0.5 wt. %, with respect to the total weight of the polymer bead. The content of acrylate copolymer less than 0.1 wt. % causes considerable deterioration in the hair setting performance of the active ingredient. The content of acrylate copolymer greater than 1.0 wt. % renders the bead so hard that the bead cannot break completely during the discharging process.

Caffeine is a whitish soft crystalline substance functioning as a stimulant of a xanthine structure with three methyl groups. According to the research studies related to hair growth, caffeine is a phosphodiesterarse inhibitor that increases the cAMP level of cells and stimulates the metabolism of derma papilla cells to accelerate the growth of follicles. Also, it inhibits the actions of testosterone, the male sex hormone incurring shrinkage of follicles to make hair fall out, and dihydrotestosterone, the active male sex hormone produced from testosterone. Yet, an excess of caffeine adversely affects derma papilla cells into necrosis, rather incurring hair loss. In the present invention, caffeine is used in an amount of 0.01 to 1.0 wt. %, preferably 0.4 to 0.6 wt. %, with respect to the total weight of the polymer bead. The content of caffeine less than 0.01 wt. % offers an insignificant effect of the caffeine for prevention of hair loss. The content of caffeine greater than 1.0 wt. % causes the dissolved caffeine to precipitate, which offers an insignificant effect of caffeine and rather incurs hair loss.

Amino acid, a compound containing basic amine ($-NH_2$) and acidic carboxyl ($-COOH$) functional groups, is used in the present invention to supply scalps with protein components through skin pores and restore damaged hair. In the present invention, amino acid is contained in an amount of 0.01 to 0.5 wt. %, preferably 0.05 to 0.2 wt. %, with respect to the total weight of the polymer bead. The content of amino acid less than 0.01 wt. % results in failure to acquire desired effects. The content of amino acid greater than 0.5 wt. % causes the dissolved amino acids to precipitate and give bad odor due to decomposition.

Keratin is the key protein component of the hair and nails. In the structure of hair keratin, helical peptide bonds, main chain bonds vertical in the lengthwise direction of hair, are stabilized with disulfide bonds, also known as cysteine bonds, horizontal side-chain bonds formed at every one of four helical turns. In the present invention, keratin is contained in an amount of 0.01 to 1.0 wt. %, preferably 0.05 to 0.2 wt. %, with respect to the total weight of the polymer bead. The content of keratin less than 0.01 wt. % leads to an insignificant effect of restoring the damaged hair. The content of keratin greater than 1.0 wt. % causes the dissolved amino acids to precipitate, making insignificant effects of keratin, and has the side-chain bonds of the hair extremely broken to rather damage the hair.

*Ulva lactuca*, a seaweed in the family Ulvaceae, has a body hardened with holdfast fronds and is used in foods or animal feeds. *Ulva lactuca* powder is a powder made from dried *Ulva lactuca* and used as an absorbent, an anti-oxidant, a binder, or a thickening agent.

Gellan gum is a polysaccharide gum substance produced from carbohydrates through axenic fermentation with seaweed-derived bacterium *Sphingomonas elodea*, purified with isopropyl alcohol, dried, and ground. It is used as a thickening agent, a stabilizer, and a gelling agent for foods. In the present invention, gellan gum is used to maintain a constant distance between beads in the aqueous phase and contained in an amount of 0.15 to 0.30 wt. % with respect to the total weight of the polymer bead. The content of gellan gum less than 0.15 wt. % causes deterioration of dispersability and hence the difficulty of discharging the bead, and the content of gellan gum greater than 0.30 wt. % results in losing the shape of the bead.

Hereinafter, a detailed description will be given as to the present invention with reference to the following examples, which are given only to exemplify the present invention and not intended to limit the scope of the present invention.

In accordance with one aspect of the composition of the present invention, there was prepared a hair essence consisting of a polymer bead and a gel.

Preparation of Bead (a1) 1.5 g of carrageenan, 0.5 g of cellulose, 0.6 g of agar, 0.1 g of charcoal powder, 0.3 g of acrylate copolymer, 0.5 g of caffeine, 0.1 g of amino acid, 0.1 g of keratin, 0.2 g of gellan gum were mixed with 96.1 g of purified water, and the mixture was homogenized under agitation at 70° C. to prepare a homogenized mixture.

(a2) The homogenized mixture was dropped on cold oil through a fog nozzle to form beads.

(a3) The beads were washed with purified water.

Preparation of Gel

TABLE 1

| Div. | Ingredients | Example (wt. %) |
|---|---|---|
| Gel component 1 | Purified water | To 100 |
| | Glyceryl glucoside | 1.5 |
| | Panthenol | 0.2 |
| | Disodium Edta | 0.1 |
| | Butyl Glycol | 3.0 |
| | Aminomethyl propanol | 0.45 |
| Gel component 2 | Acrylate, $C_{10-30}$ alkylacrylate cross-polymer | 0.5 |
| Gel component 3 | Preservative | 0.5 |
| | Menthol | 0.3 |
| | Salicylic acid | 0.25 |
| | Ethanol | 10.0 |
| | PEG-60 hydrogenated castor oil | 1.5 |
| | Polysorbate 80 | 1.5 |

(b1) 7.5 g of glyceryl glucoside, 1 g of panthenol, 0.5 g of disodium Edta, 15 g of butylene glycol, and 2.25 g of aminomethylpropanol were mixed with purified water, and the mixture was homogenized under agitation at 70° C. to prepare a homogenized mixture 1.

(b2) 2.5 g of acrylate was added to the homogenized mixture 1 under sustained agitation at 70° C. to prepare a homogenized mixture 2.

(b3) 2.5 g of a preservative, 1.5 g of menthol, 1.25 g of salicylic acid, 50 g of ethanol, 7.5 g of PEG-60 hydrogenated castor oil, and 7.5 g of polysorbate 80 were mixed with purified water to the total weight of 500 g under sustained agitation to form a gel.

(b4) Beads were added to the gel, and the mixture was then homogenized.

Figure 2:
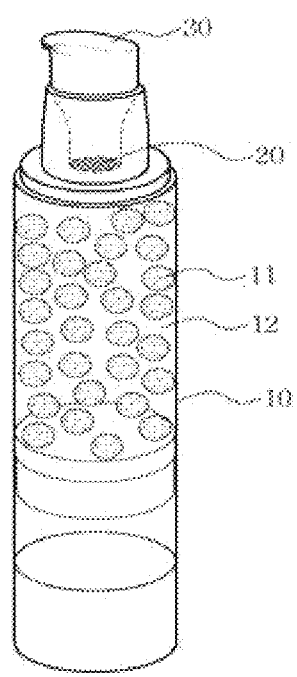
FIG. 2 shows the shape of a container containing the composition of the present invention.

The beads thus obtained were filled in a vacuum container equipped with an airless pump while a constant bead-to-bead distance was maintained on the gel (FIG. 2). With the pump of the container ON, the beads together with the gel were forced to pass through a mesh provided in the pumping portion of the container and discharged out of the container. During this process, the beads completely lost their shape by the mesh and got mixed with the gel.

Hardness Measurement of Beads

TABLE 2

| | | | | Unit: wt. % |
|---|---|---|---|---|
| | Example | Comparative Example | | |
| Div. | 1 | 1 | 2 | 3 |
| Carrageenan | 1.5 | 0.5 | 1.5 | 1.5 |
| Cellulose | 0.5 | 0.5 | 0.5 | 0.5 |
| Agar | 0.6 | 0.6 | 2.5 | 0.6 |

TABLE 2-continued

|  | Example | Comparative Example | | Unit: wt. % |
| --- | --- | --- | --- | --- |
| Div. | 1 | 1 | 2 | 3 |
| Charcoal powder | 0.1 | 0.1 | 0.1 | 0.1 |
| Acrylate copolymer | 0.3 | 0.3 | 0.3 | 1.5 |
| Caffeine | 0.5 | 0.5 | 0.5 | 0.5 |
| Amino acid | 0.1 | 0.1 | 0.1 | 0.1 |
| Keratin | 0.1 | 0.1 | 0.1 | 0.1 |
| Gellan gum | 0.2 | 0.2 | 0.2 | 0.2 |
| Purified water | To 100 | To 100 | To 100 | To 100 |
| Average hardness (g) | 570 | 980 | 1,020 | 950 |

The beads prepared according to the Example 1 and the Comparative Examples 1, 2 and 3 were measured in regards to the hardness with a compression tester (FGC-01 Shimpo, Japan), and the hardness measurements were averaged as presented in table 3. The Comparative Examples 1, 2 and 3 showed that the beads had such a high hardness to stop discharging from the container by the mesh provided in the inlet of the pumping portion. In the Example 1, on the other hand, the beads completely lost their shape by the presence of the mesh during discharge and got mixed with the gel, so the active ingredient in the beads was applied to the hair effectively.

Correlation Between Mesh Area and Size and Hardness of Beads (1) Mesh area: less than 0.25 mm$^2$

TABLE 3

|  |  | Size of beads (D) | | |
| --- | --- | --- | --- | --- |
|  |  | 2 mm ≤ D ≤ 6 mm | 6 mm ≤ D ≤ 10 mm | 10 mm ≤ D ≤ 14 mm |
| Hardness of bead | <400 g | 8 | 3 | 3 |
|  | 400-700 g | 9 | 5 | 5 |
|  | >700 g | 7 | 1 | 1 |

Note:
1 = Beads are extremely unmixable with the gel through the mesh due to high hardness and large bead size relative to the mesh size.
2 = Beads are unmixable with the gel through the mesh due high hardness, albeit with small bead size relative to the mesh size.
3 = Beads are unable to keep their shape due to low hardness and large bead size relative to the mesh size.
4 = Beads are unable to keep their shape due to low hardness and small bead size relative to the mesh size.
5 = Beads are unmixable with the gel through the mesh due to large bead size, albeit with moderate hardness.
6 = Beads are unmixable with the gel through the mesh due to small bead size, albeit with moderate hardness.
7 = Beads are unmixable with the gel through the mesh due to high hardness, albeit with moderate bead size.
8 = Beads are unable to keep their shape due to low hardness, albeit with moderate bead size.
9 = Beads are well mixed with the gel through the mesh due to moderate hardness and moderate bead size relative to the mesh size.

(2) Mesh area: between 0.25 mm$^2$ and 1 mm$^2$

TABLE 4

|  |  | Size of beads (D) | | |
| --- | --- | --- | --- | --- |
|  |  | 2 mm ≤ D ≤ 6 mm | 6 mm ≤ D ≤ 10 mm | 10 mm ≤ D ≤ 14 mm |
| Hardness of bead | <400 g | 4 | 8 | 3 |
|  | 400-700 g | 6 | 9 | 5 |
|  | >700 g | 2 | 7 | 1 |

Note:
1 = Beads are extremely unmixable with the gel through the mesh due to high hardness and large bead size relative to the mesh size.
2 = Beads are unmixable with the gel through the mesh due high hardness, albeit with small bead size relative to the mesh size.
3 = Beads are unable to keep their shape due to low hardness and large bead size relative to the mesh size.
4 = Beads are unable to keep their shape due to low hardness and small bead size relative to the mesh size.
5 = Beads are unmixable with the gel through the mesh due to large bead size, albeit with moderate hardness.
6 = Beads are unmixable with the gel through the mesh due to small bead size, albeit with moderate hardness.
7 = Beads are unmixable with the gel through the mesh due to high hardness, albeit with moderate bead size.
8 = Beads are unable to keep their shape due to low hardness, albeit with moderate bead size.
9 = Beads are well mixed with the gel through the mesh due to moderate hardness and moderate bead size relative to the mesh size.

(3) Mesh area: greater than 1 mm$^2$

TABLE 5

|  |  | Size of beads (D) | | |
| --- | --- | --- | --- | --- |
|  |  | 2 mm ≤ D ≤ 6 mm | 6 mm ≤ D ≤ 10 mm | 10 mm ≤ D ≤ 14 mm |
| Hardness of bead | <400 g | 4 | 4 | 8 |
|  | 400-700 g | 6 | 6 | 9 |
|  | >700 g | 2 | 2 | 7 |

Note:
1 = Beads are extremely unmixable with the gel through the mesh due to high hardness and large bead size relative to the mesh size.
2 = Beads are unmixable with the gel through the mesh due high hardness, albeit with small bead size relative to the mesh size.
3 = Beads are unable to keep their shape due to low hardness and large bead size relative to the mesh size.
4 = Beads are unable to keep their shape due to low hardness and small bead size relative to the mesh size.
5 = Beads are unmixable with the gel through the mesh due to large bead size, albeit with moderate hardness.
6 = Beads are unmixable with the gel through the mesh due to small bead size, albeit with moderate hardness.
7 = Beads are unmixable with the gel through the mesh due to high hardness, albeit with moderate bead size.
8 = Beads are unable to keep their shape due to low hardness, albeit with moderate bead size.
9 = Beads are well mixed with the gel through the mesh due to moderate hardness and moderate bead size relative to the mesh size.

A comparison of the examples shows that when the mesh size is less than 0.25 mm$^2$, the beads, if having a size of 2 mm or greater and less than 6 mm and a hardness of 400 to 700 g, completely broke to lose their shape while passing through the mesh during the discharge out of the container and became well mixed with the gel.

With the mesh size of 0.25 mm$^2$ to 1 mm$^2$, the beads having a size of 6 mm or greater and less than 10 mm and a hardness of 400 to 700 g were well mixed with the gel. Further, when the mesh size was 1 mm$^2$ or greater, the beads having a size of 10 mm or greater and less than 14 mm and a hardness of 400 to 700 g, were well mixed with the gel to provide the desired functions.

Measurement of Average Hair Thickness 10 female volunteers in their 20s were asked to use an air essence containing the composition of the present invention (90 wt. % gel+10 wt. % bead) as an active ingredient for the investigation of the average hair thickness. The measurement of hair thickness was carried out with Armo TS-2 model (Aram Huvis Co., Ltd.) for the female volunteers with healthy hair neither permed nor colored. The measurement results are presented in the following Table 6 and FIG. 1.

TABLE 6

| Div. | Before application | 2 weeks after application | Rate of increase |
|---|---|---|---|
| 1 | 74 μm | 77 μm | 2.2% |
| 2 | 81 μm | 85 μm | 3.2% |
| 3 | 79 μm | 84 μm | 4.0% |
| 4 | 88 μm | 90 μm | 1.8% |
| 5 | 78 μm | 82 μm | 3.1% |
| 6 | 85 μm | 88 μm | 2.6% |
| 7 | 79 μm | 82 μm | 2.4% |
| 8 | 75 μm | 77 μm | 1.5% |
| 9 | 72 μm | 75 μm | 2.2% |
| 10 | 81 μm | 84 μm | 2.4% |
| Average rate of increase | | | 2.5% |

The female volunteers participated in a first measurement for hair thickness before application of the hair essence containing the composition of the present invention as an active ingredient and a second measurement 2 weeks after the application. According to the measurement results, the hair thickness increased by about 2.5% with the color of hair changed to black (refer to FIG. 1).

Hair essence products containing the composition of the present invention with different bead contents were applied to 20 male and female volunteers. The hair thickness measurements were averaged and presented in the following Table 7.

TABLE 7

| | Example 2 | Example 3 | Comparative Example 5 |
|---|---|---|---|
| Composition | 97 wt. % gel + 3 wt. % bead | 90 wt. % gel + 10 wt. % bead | 100 wt. % gel |
| Average hair thickness before application | 77 μm | 79 μm | 80 μm |
| Average hair thickness 2 weeks after application | 79 μm | 82 μm | 81 μm |
| Rate of increase (%) | About 1.5% | About 2.4% | About 0.8% |

Armo TS-2 model (Aram Huvis Co., Ltd.) was used to determine the rate of increase in the hair thickness as a function of the weight ratio of the beads. According to the measurement results, the application of the hair essence containing 100 wt. % of gel without beads increased the thick thickness by no more than about 0.8%; whereas about 1.5% of the increment in the hair thickness resulted from the application of the hair essence containing 3 wt. % of beads and about 2.4% of the increment in the hair thickness was from the application of the hair essence containing 10 wt. % of beads.

What is claimed is:

1. A composition for preventing hair loss and thickening hair, comprising a bead as an active ingredient,
   the bead comprising 1.0 to 2.0 wt. % of carrageenan, 0.1 to 1.0 wt. % of cellulose, 0.1 to 2.0 wt. % of agar, 0.01 to 0.5 wt. % of charcoal powder, 0.1 to 1.0 wt. % of acrylate copolymer, 0.01 to 1.0 wt. % of caffeine, 0.01 to 0.5 wt. % of amino acid, 0.01 to 1.0 wt. % of keratin, 0.15 to 0.3 wt. % of gellan gum, and purified water.

2. The composition as claimed in claim 1, wherein the bead further comprises at least one active ingredient selected from the group consisting of *Ulva lactuca* extract powder, L-menthol, salicylic acid, dexpanthenol, niacinamide, zinc pyrithione, and biotin.

3. The composition as claimed in claim 1, wherein the composition comprises the bead and a gel,
   wherein the bead is contained in an amount of 3 to 10 wt. % with respect to 100 wt. % of the composition.

4. The composition as claimed in claim 3, wherein the gel comprises 1.5 wt. % of glyceryl glucoside, 0.2 wt. % of panthenol, 0.1 wt. % of disodium EDTA, 3.0 wt. % of butylene glycol, 0.45 wt. % of aminomethylpropanol, 0.5 wt. % of acrylate, 0.5 wt. % of a preservative, 0.3 wt. % of menthol, 0.25 wt. % of salicylic acid, 10.0 wt. % of ethanol, 1.5 wt. % of PEG-60 hydrogenated castor oil, 1.5 wt. % of polysorbate 80, and purified water.

5. The composition as claimed in claim 3, wherein the bead has an average diameter of 6 to 10 mm,
   wherein the bead is forced to pass through a mesh with a mesh area of 0.25 to 1 mm$^2$ and lose a shape thereof and thus mixed with the gel.

6. The composition as claimed in claim 1, wherein the composition is provided as a formulation type selected from the group consisting of hair toner, hair lotion, hair cream, hair spray, hair mousse, hair gel, hair soap, hair shampoo, hair conditioner, hair massage pack, and hair treatment.

7. A method for preparing a composition for preventing hair loss and thickening hair, comprising a bead as an active ingredient,
   wherein the bead is prepared in the steps of:
   (a1) mixing, with respect to 100 wt. % of the bead, 1.0 to 2.0 wt. % of carrageenan, 0.1 to 1.0 wt. % of cellulose, 0.1 to 2.0 wt. % of agar, 0.01 to 0.5 wt. % of charcoal powder, 0.1 to 1.0 wt. % of acrylate copolymer, 0.01 to 1.0 wt. % of caffeine, 0.01 to 0.5 wt. % of amino acid, 0.01 to 1.0 wt. % of keratin, and 0.15 to 0.3 wt. % of gellan gum with purified water to obtain a mixture and homogenizing the mixture under agitation at 70° C.;
   (a2) dropping the homogenized mixture on cold oil through a fog nozzle to form a bead; and
   (a3) washing the bead with purified water.

8. A method for preparing a composition for preventing hair loss and thickening hair, comprising:
   (b1) mixing, with respect to 100 wt. % of gel, 1.5 wt. % of glyceryl glucoside, 0.2 wt. % of panthenol, 0.1 wt. % of disodium EDTA, 3.0 wt. % of butylene glycol, and 0.45 wt. % of aminomethylpropanol with purified water to obtain a mixture and homogenizing the mixture under agitation at 70° C. to prepare a homogenized mixture 1;
   (b2) adding 0.5 wt. % of acrylate with respect to 100 wt. % of the gel to the homogenized mixture 1 under sustained agitation at 70° C. to prepare a homogenized mixture 2;
   (b3) adding, with respect to 100 wt. % of the gel, 0.5 wt. % of a preservative, 0.3 wt. % of menthol, 0.25 wt. % of salicylic acid, 10.0 wt. % of ethanol, 1.5 wt. % of PEG-60 hydrogenated castor oil, 1.5 wt. % of polysorbate 80, and purified water and mixing under sustained agitation to form a gel; and
   (b4) adding beads to the gel and uniformly mixing the beads and the gel together.

9. The method as claimed in claim 8, wherein the beads have an average diameter of 6 to 10 mm,
   wherein the beads are forced to pass through a mesh with a mesh area of 0.25 to 1 mm$^2$ and lose a shape thereof and thus mixed with the gel.

* * * * *